United States Patent [19]

Shirafuji et al.

[11] Patent Number: 4,849,550
[45] Date of Patent: Jul. 18, 1989

[54] METHOD FOR PRODUCING CYCLOALKANOLS

[75] Inventors: Tamio Shirafuji; Itaru Kawata, both of Niihama, Japan

[73] Assignee: Sumitomo Chemical Company, Limited, Osaka, Japan

[21] Appl. No.: 172,386

[22] Filed: Mar. 24, 1988

[30] Foreign Application Priority Data

Apr. 8, 1987 [JP] Japan ................................. 62-87627

[51] Int. Cl.4 ........................ C07C 29/04; C07C 29/06
[52] U.S. Cl. .................................... 568/899; 568/821; 568/822; 568/835; 568/838; 568/895
[58] Field of Search ............... 568/821, 822, 835, 838, 568/895

[56] References Cited

U.S. PATENT DOCUMENTS

| 3,528,409 | 7/1970 | Mitsui et al. | 568/899 |
| 4,306,101 | 12/1981 | Slaugh et al. | 568/899 |
| 4,595,786 | 6/1986 | Waller | 568/835 |
| 4,691,064 | 9/1987 | Shirafuji et al. | 568/895 |
| 4,716,253 | 12/1987 | Shirafuji et al. | 568/895 |

OTHER PUBLICATIONS

Tanabe, "Cablysis Science and Technology", vol. 2, Chapter 5, New York (1981), pp. 232–234.

*Primary Examiner*—Werren B. Lone
*Attorney, Agent, or Firm*—Stevens, Davis, Miller & Mosher

[57] ABSTRACT

A industrially excellent method for producing a cycloalkanol by the hydration of a cycloalkene having from 4 to 8 carbon atoms with an aromatic sulfonic acid as a catalyst which comprises carrying out said hydration in the presence of a phenol.

3 Claims, No Drawings

METHOD FOR PRODUCING CYCLOALKANOLS

The present invention relates to a method for producing cycloalkanols, and more particularly, to a method for producing cycloalkanols by hydrating cycloalkenes with aromatic sulfonic acids as a catalyst.

For producing cycloalkanols by the hydration of cycloalkenes, methods of using various catalysts are known.

A method of using mineral acids, particularly sulfuric acid is a well known method.

A method of using heteropoly acids such as phosphotungstic acid, phosphomolybdic acid, etc. is disclosed in JP-B-No.58-1089.

Also, JP-B-NO.43-8104 and JP-B-No.43-16125 discloses a method of using aromatic sulfonic acids as a catalyst.

Further, there are known a method of using solid catalysts wherein a mineral acid has been supported on a carrier and a method of using cation exchange resins (JP-B-No.38-15619, JP-B-No.44-26656) and a method of using zeolite (JP-B-No.47-45323).

In the method of using sulfuric acid, a sulfuric acid ester is formed together with a desired cycloalkanol. This ester is hydrolyzed into sulfuric acid and cycloalkanol, after which the latter is recovered, so that the operation becomes troublesome.

In the method of using heteropoly acids, the conversion is as low as several %.

In the methods of using solid catalysts such as cation exchange resins and zeolite, the life of the catalysts becomes a problem, so that the catalysts cannot maintain stabilized activity for a long period of time.

When aromatic sulfonic acids are used in JP-B-No.43-8104, the sulfonic acid is used in a concentration as high as 1.5 by the weight ratio of sulfonic acid to water, but the conversion of cyclohexene is as low as from several % to 20%. Also, in JP-B-No.43-16125, the sulfonic acid is used in a concentration as further high as 4.5 by the weight ratio of sulfonic acid to water, but the conversion of cyclohexene is only 30%.

In the method to produce cycloalkanols by the hydration of cycloalkenes, the present inventors extensively studied to find a method which is economic and yet gives high yields, and as a result, completed the present invention.

The present invention provides a method for producing cycloalkanols by the hydration of cycloalkenes with aromatic sulfonic acids as a catalyst characterized in that said hydration is carried out in the presence of a phenol.

According to the present invention, a large increase in the conversion is obtained as compared with a case wherein a phenol is not present.

The cycloalkenes used in the present invention include cyclobutene, cyclopentene, cyclohexene, cycloheptene, cyclooctene, methylcyclopentene, methylcyclohexene, methylcycloheptene, dimethylcyclohexene, etc.

The phenols used in the present invention refer to phenol and substituted phenols, being a compound having one or more hydroxyl groups directly bonded to the aromatic ring.

Specifically, there are given phenol, cresol, xylenol, ethylphenol, trimethylphenol, isopropylphenol, chlorophenol, phenylphenol, nitrophenol, tert-butylphenol, salicylic acid, pyrocatechol, 2-naphthol, etc.

The amount of these phenols used is from about 0.01 to about 10 parts by weight, preferably from 0.1 to 2 parts by weight based on the cycloalkenes which are a material.

The aromatic sulfonic acid used as a catalyst is not particularly limited, and its examples include p-toluenesulfonic acid, benzenesulfonic acid, p-phenol-sulfonic acid, sulfosalicylic acid, 2-naphtholsulfonic acid, etc.

As to the catalyst concentration in the present invention, a higher catalyst concentration in the aqueous solution is more preferred. The catalyst is used as an aqueous solution of usually from about 10% to about 80% by weight, preferably from 30% to 70% by weight.

The amount of the catalyst used in the present invention cannot be determined indiscriminately, because it depends largely upon the reaction form. Usually, however, a range of from about 0.1 to about 100 parts by weight based on 1 part by weight of the cycloalkene is preferably used. When the amount of catalyst is less than 0.1 part by weight based on 1 part by weight of the cycloalkene, the rate of reaction is low. While even amounts more than 100 parts by weight give no sufficient effect enough to correspond to so large amounts.

The reaction temperature in the present invention is in a range of from about 30° to about 300° C., particularly preferably from 70° to 180° C.

The reaction may be carried out either at normal pressure or under pressure.

The reaction form may be any of a batch form and continuous form.

However, when hydration is carried out in the presence of a phenol as in the present invention, the selectivity of cycloalkanol at one pass somewhat lowers as compared with a case wherein a phenol is not present.

This may be considered to be due to that a phenol reacts with cycloalkenes to produce ethers.

The present inventors studied about these ethers and found that the formation of ethers is an equilibrium reaction.

For example, when cyclohexene is used as a cycloalkene and m-cresol is used as a phenol, there is an equilibrium relation shown by the following equation (1) between, on one hand, cyclohexene and m-cresol and on the other hand, tolyl cyclohexyl ether produced therefrom (hereinafter referred to as TCE):

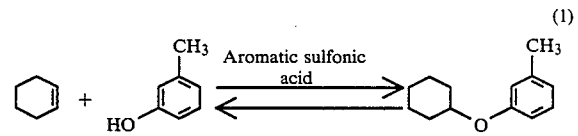

(1)

In the cycloalkanol manufacturing method by the continuous form, a cycloalkene is hydrated, after which the oily phase and aqueous phase are separated from each other. The unreacted cycloalkene and cycloalkanol are separated from this oily phase, and the residual phenol and the other, a by-product, are circulated as they are to hydration. If this circulation is repeated, the amount of the ether newly formed as by-product decreases gradually by the equilibrium relation shown by the equation (1) and reaches an equilibrium at a definite concentration. Consequently, when this circulation form is used, a difference in the selectivity of cycloalkanol owing to the presence and absence of a phenol becomes unrecognized.

Even in the batch form, if the ether is added in advance, the difference in selectivity is not likewise recognized.

The method of the present invention, as compared with a case wherein an aromatic sulfonic acid alone is used, can markedly increase the conversion of hydration of cycloalkenes by adding a phenol, so that it is an industrially excellent method.

The present invention will be illustrated more specifically with reference to the following examples, but it is not limited to these examples.

EXAMPLE 1

To a 1-liter pressure-proof glass autoclave were added 150 g of cyclohexene, 270 g of water and 270 g of p-toluenesulfonic acid, after which 150 g of m-cresol was added. After replacing the gaseous phase in the autoclave by nitrogen, reaction was carried out at 120° C. for 2 hours.

After completion of the reaction, the reaction solution was analyzed by gas chromatography, and it was found that the conversion of cyclohexene was 64% and the selectivity of cyclohexanol was 91%.

COMPARATIVE EXAMPLE 1

Reaction was carried out in the same manner as in Example 1 except that m-cresol was not added, and it was found that the conversion of cyclohexene was 32% and the selectivity of cyclohexanol was 97%.

EXAMPLES 2 TO 4

To a 1-liter pressure-proof glass autoclave were added 150 g of cyclohexene, 300 g of water and 300 g of p-toluenesulfonic acid, after which a prescribed amount of phenol was added. After replacing the gaseous phase in the autoclave by nitrogen, reaction was carried out at 120° C. for 2 hours.

After completion of the reaction, the reaction solution was analyzed by gas chromatography. The results are shown in Table 1.

TABLE 1

| Example No. | Amount of phenol added (g) | Conversion of cyclohexene (%) | Selectivity of cyclohexanol (%) |
|---|---|---|---|
| 2 | 37 | 43 | 95 |
| 3 | 75 | 50 | 94 |
| 4 | 150 | 64 | 91 |

EXAMPLES 5 TO 7

Reaction was carried out in the same manner as in Example 1 except that the kind of a phenol was changed. The results are shown in Table 2.

TABLE 2

| Example No. | Phenol | Conversion of cyclohexene (%) | Selectivity of cyclohexanol (%) |
|---|---|---|---|
| 5 | Pyrocatechol | 71 | 88 |
| 6 | o-Cresol | 54 | 92 |
| 7 | 2,6-xylenol | 37 | 96 |

EXAMPLE 8

To a 1-liter pressure-proof glass autoclave were added 150 g of cyclohexene, 300 g of water and 300 g of 2-naphtholsulfonic acid, after which 150 g of m-cresol was added. After replacing the gaseous phase in the autoclave by nitrogen, reaction was carried out at 120° C. for 3 hours.

As a result, it was found that the conversion of cyclohexene was 49% and the selectivity of cyclohexanol was 94%.

COMPARATIVE EXAMPLE 2

Reaction was carried out in the same manner as in Example 8 except that m-cresol was not added. As a result, it was found that the conversion of cyclohexene was 31% and the selectivity of cyclohexanol was 96%.

REFERENCE EXAMPLE

To a 1-liter pressure-proof glass autoclave were added 150 g of cyclohexene, 360 g of water, 240 g of 2-naphtholsulfonic acid and 75 g of m-cresol, and then a prescribed amount of tolyl cyclohexyl ether (TCE) was added. Reaction was carried out in the same manner as in Example 1.

The amount of TCE which changed before and after reaction is shown in Table 3.

TABLE 3

| No. | A : Amount of TCE added (g) | B : Amount of TCE after reaction (g) | B - A (g) |
|---|---|---|---|
| 1 | 0 | 0.8 | 0.8 |
| 2 | 5.0 | 5.6 | 0.6 |
| 3 | 9.2 | 9.6 | 0.4 |
| 4 | 27.2 | 26.4 | −0.8 |

Table 3 shows that the formation of TCE decreases with increasing amount of TCE added, and that when a further large amount of TCE is added, TCE added decomposes, which means that the formation of TCE reaches an equilibrium at a definite concentration.

What is claimed is:

1. A method for producing a cycloalkanol having from 4 to 8 carbon atoms by the hydration of a cycloalkene having from 4 to 8 carbon atoms with water using an aromatic sulfonic acid in solution in the water as a catalyst, which comprises carrying out said hydration at a temperature of from about 30° C. to about 300° C. in the presence of at least one phenol selected from the group consisting of phenol, cresol, xylenol and pyrocatechol.

2. A method according to claim 1, wherein the amount of the phenol is from 0.01 to 10 parts by weight based on 1 part by weight of the cycloalkene.

3. A method according to claim 1, wherein the cycloalkene is cyclohexene.

* * * * *